United States Patent [19]

Liang et al.

[11] Patent Number: 5,570,404
[45] Date of Patent: Oct. 29, 1996

[54] METHOD AND APPARATUS FOR EDITING ABDOMINAL CT ANGIOGRAPHIC IMAGES FOR BLOOD VESSEL VISUALIZATION

[75] Inventors: Cheng-Chung Liang, Lawrenceville; Ajit Singh, Plainsboro; Ming-Yee Chiu, Princeton Junction; Jay Ezrielev, Jersey City; Richard Fisler, Kendall Park; Dietmar Hentschel, Little Silver, all of N.J.

[73] Assignee: Siemens Corporate Research, Princeton, N.J.

[21] Appl. No.: 315,524

[22] Filed: Sep. 30, 1994

[51] Int. Cl.⁶ ..................................................... A61B 6/03
[52] U.S. Cl. .......................... 378/8; 378/901; 364/413.19
[58] Field of Search ........................... 378/8, 98.12, 210, 378/901; 250/363.04; 364/413.19, 413.23

[56] References Cited

U.S. PATENT DOCUMENTS 4,709,385  11/1987  Pfeiler et al. ......................... 378/98.12
5,243,664   9/1993  Tuy ............................................ 382/6

OTHER PUBLICATIONS

"Editing Tools for 3D Medical Imaging", Ney et al., IEEE Computer Graphics & Applications, Nov. 1991, pp. 63–71.
"An Image Editor for a 3D–CT Reconstruction System", Ezrielev et al, SPIE vol. 1233, Medical Imaging IV: Image Processing (1990), pp. 67–76.

Primary Examiner—David P. Porta
Assistant Examiner—David Vernon Bruce
Attorney, Agent, or Firm—Adel A. Ahmed

[57] ABSTRACT

A method for automatically editing a plurality of CT image slices to provide a three dimensional view of a selected object located within a patient's body comprises providing at least one slab of CT image slices produced by CT scanning system and computing a top MIP image of the slab. An undesirable object is automatically removed from the top MIP image by first detecting all the pixels having illuminating intensity values which represent the undesirable object. Then all the pixels of the object to be removed are set to a substantially zero illuminating intensity value in order to remove the object from the top MIP image of the slab. After the undesirable object is removed from the top MIP image, the edits made thereto are applied to each CT image slice in the slab. The present invention also includes apparatus for performing a 3D reconstruction of CT angiographic images to visualize a selected object located within a patient's body. The apparatus comprises an x-ray tube for projecting energy into a layer of interest in the patient's body and a detector for detecting changes in the projected energy as it exits the layer of interest. The changes detected in the projected energy are indicative of various objects including the selected object that are located within the layer of interest of the patient's body. Moreover, the x-ray tube and detector operate in conjunction to provide at least one slab of CT image slices.

20 Claims, 18 Drawing Sheets

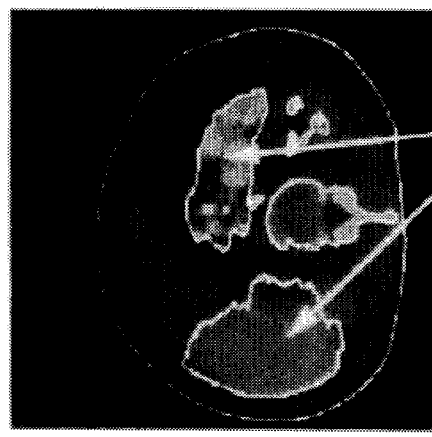
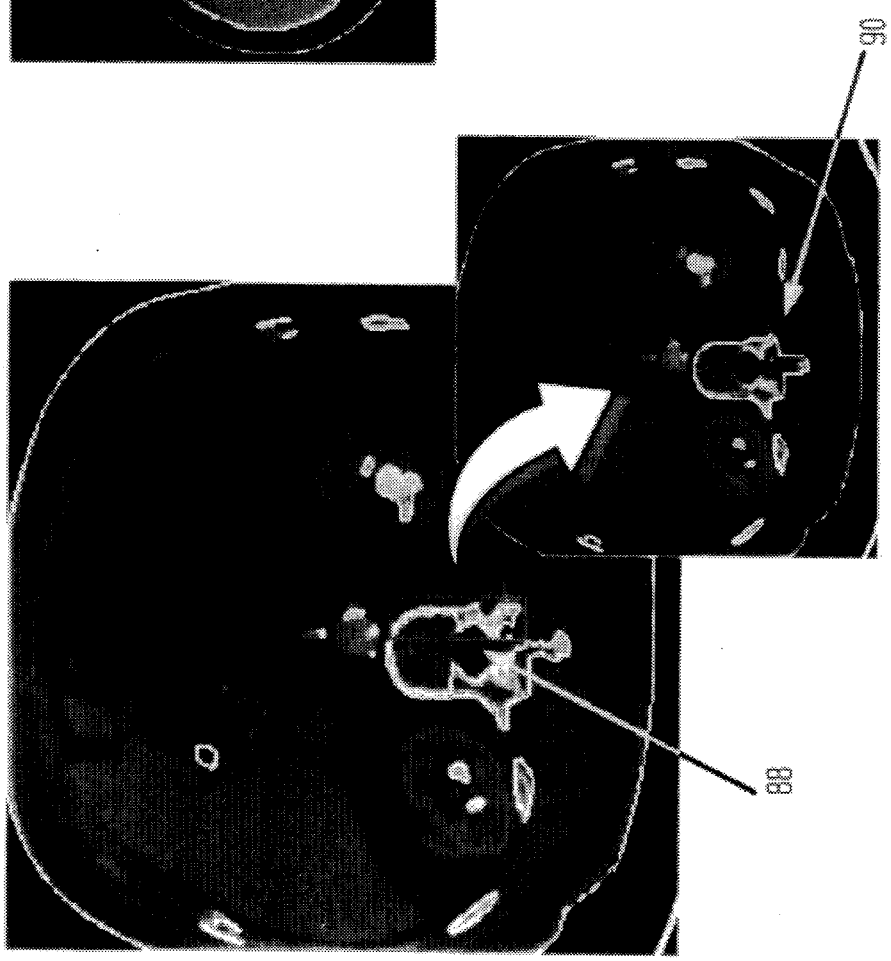

METHOD AND APPARATUS FOR EDITING ABDOMINAL CT ANGIOGRAPHIC IMAGES FOR BLOOD VESSEL VISUALIZATION

FIELD OF INVENTION

This invention relates generally to computed tomography and more particularly to a method and apparatus for automatically outlining regions of interest on computed tomograms used for three dimensional reconstruction of image data acquired from abdominal computed tomographic angiography.

BACKGROUND OF THE INVENTION

Computed tomography (CT) produces two-dimensional (2D) axial transverse tomograms which are images of body layers that are oriented essentially perpendicular to the longitudinal axis of the body. Recently, methods for three-dimensional (3D) reconstruction of image data acquired from CT scanners have been developed. Methods employing 3D reconstruction of computed tomograms to visualize blood vessels have many potential new applications in medical diagnosis. Such methods provide data sets of vascular information from a sequence of computed tomograms which represent a 3D volume.

Maximum Intensity Projection (MIP) is a commonly used technique for displaying 3D vascular image data. MIP relies on the blood in the vessel having a higher pixel intensity value than other organs of the imaged anatomy. This relationship, however, does not apply to certain types of tissues. In a CT image, for instance, the pixel intensity of bones tends to be of a higher value than that of the blood vessels. Thus, in many instances in order to correctly display the blood vessels in a 3D reconstruction of CT image data, structures having pixel intensity values similar or higher than that of blood vessels must be removed by editing.

Undesirable structures are most reliably removed using prior art manual editing methods. These methods employ an expert who manually draws outlines of the structures to be removed on every image slice using careful hand-directed cursor manipulations. The major disadvantage of such methods is that manual editing is a very repetitive process. When the number of image slices to be edited is large, as in a typical study to be 3D reconstructed using CT imaging, manual editing consumes expensive machine and operator time, notwithstanding that the operator is an expert.

Numerous interactive schemes and methods have been proposed in the prior art for helping users edit images more efficiently. One example of such a method is described in an article entitled AN IMAGE EDITOR FOR A 3D-CT RECONSTRUCTION SYSTEM by Jay Ezrielev et al. published in Proceedings of Medical Imaging IV, Image Processing, Newport Beach, 1990, Vol. 1233. The authors of this article discuss an image editing system which utilizes intelligent and semi-automated methods to improve the speed and efficiency of the editing process. Some functions are provided in their editing system which operate on entire image sets instead of individual images. These functions are capable of accomplishing thresholding operations or operations that remove simple objects from the data set. Manual editing functions are also provided to accomplish operations that the semi-automated methods are not capable of performing.

Another CT image editing method is described in an article published in IEEE Computer Graphics and Applications, November 1991, entitled EDITING TOOLS FOR 3D MEDICAL IMAGING by Derek R. Ney et al. In this article, the authors present an editing method which is patterned after a paint and drawing program. This editing method lets the user interactively create shapes manually which are used to define volumes of interest to be edited in images of medical data.

These and other methods, however, are still not capable of relieving the user from the time consuming and tedious editing process of manually drawing regions of interest to be edited from the image slices. More recently, however, a quick and user-friendly interactive editing method has been developed which facilitates the process of removing undesirable structures from image slices used in 3D reconstruction. This editing method makes use of the ability to view several consecutive images as one superimposed image. This method generally involves defining the desired modifications on the superimposed image and then applying these modifications to the individual images slices. This saves much time and effort by avoiding the need to individually edit each image.

Specifically, this method involves modifying a stack of images to remove certain tissues such as bones and uses the modified images for the 3D visualization of blood vessels. The stack of images is subdivided into a number of subsets or slabs. For each slab, a superimposed image is computed by applying an MIP algorithm to the image data of the slab. The computed superimposed image is commonly referred to as a top MIP image. The user manually makes modifications to the top MIP image of every slab. These modifications are then applied to every image in the slab from which the top MIP image is derived.

The top MIP image can be edited in a number of ways. A user can manually draw contours around the regions to be removed or retained. The user can also edit the individual images to supplement the modifications made to the top MIP image. All the slabs of the stack are sequentially traversed during the editing process, such that the current slab inherits the contours of the previously modified slab. Thus, the user can adjust the inherited contours on the top MIP image of the third slab instead of having to draw them from scratch.

Although the prior art editing method described above is a very significant improvement over earlier editing methods, it still requires the user to manually outline regions of interest by hand. The continuing necessity to perform manual editing in the aforementioned prior art method ultimately limits the speed of the editing process. Hence, there remains a need for further improvements in the speed of the editing for 3D reconstruction imaging.

It is, therefore, a primary object of the present invention to increase the editing speed of abdominal CT angiography images used for 3D blood vessel visualization. This is accomplished by providing a novel editing method for automatically outlining regions to be removed from the CT images.

SUMMARY OF THE INVENTION

The invention relates to a method for automatically editing a plurality of CT image slices to provide a three dimensional view of a selected object located within a patient's body. Each CT image slice is comprised of an array of pixels having various illuminating intensity values which are indicative of various objects scanned by a CT scanning system.

The method comprises providing at least one slab of CT image slices produced by CT scanning system and computing a top MIP image of the slab. An undesirable object is automatically removed from the top MIP image by first detecting all the pixels having illuminating intensity values which represent the undesirable object. Then all the pixels of the object to be removed are set to a substantially zero illuminating intensity value in order to remove the object from the top MIP image of the slab.

After the undesirable object is removed from the top MIP image, the edits made thereto are applied to each CT image slice in the slab.

Automatic editing of the top MIP of each slab offers great improvements in the speed of editing which reduces operator and machine time.

The present invention also includes apparatus for performing a 3D reconstruction of CT angiographic images to visualize a selected object located within a patient's body. The apparatus comprises means for projecting energy into a layer of interest in the patient's body and means for detecting changes in the projected energy as it exits the layer of interest.

The changes detected in the projected energy are indicative of various objects including the selected object that are located within the layer interest of the patient's body. Moreover, the projecting means and detecting means operate in conjunction to provide at least one slab of CT image slices.

The apparatus further includes means for automatically editing an undesirable object from a top MIP image of a slab of CT image slices and applying the edits to each individual CT image slice in the slab in order to freely visualize the selected object in 3D.

BRIEF DESCRIPTION OF THE DRAWINGS

The methods and apparatus for automatically outlining regions of interest to be removed from a slab of CT image slices used for 3D abdominal CT angiography according to the present invention, will be better understood from the following description, claims and appended drawings in which:

FIG. 9A is a graphical example of a region that is narrower than the main vertebral region;

FIG. 9B is a graphical example of merging the region shown in FIG. 9A into the main vertebral region;

FIG. 9C is a graphical example of regions that are larger than the main vertebral region;

FIG. 15A illustrates the image before applying the masks and FIG. 15B illustrates the image after the application of the masks;

DETAILED DESCRIPTION OF THE INVENTION

The present invention is directed at a method for automatically editing images used in abdominal 3D-CT angiography. The method provides automatic outlining of regions to be removed and offers great improvements in the speed of the editing. Although the present invention is intended for 3D-CT imaging of the abdominal area it is contemplated that the present invention can also be adapted for use in 3D-CT imaging of other areas of the body and/or adapted for use with other imaging techniques such as MRI.

The present invention applies the concepts of the prior art editing method described immediately above and improves upon it by providing an automatic scheme for outlining regions of interest especially as they relate to the abdominal area.

As briefly described earlier, the aforementioned prior art editing method generally involves manually making modifications on a top MIP image which has been computed from a slab comprising several consecutive images.

Figure 1:
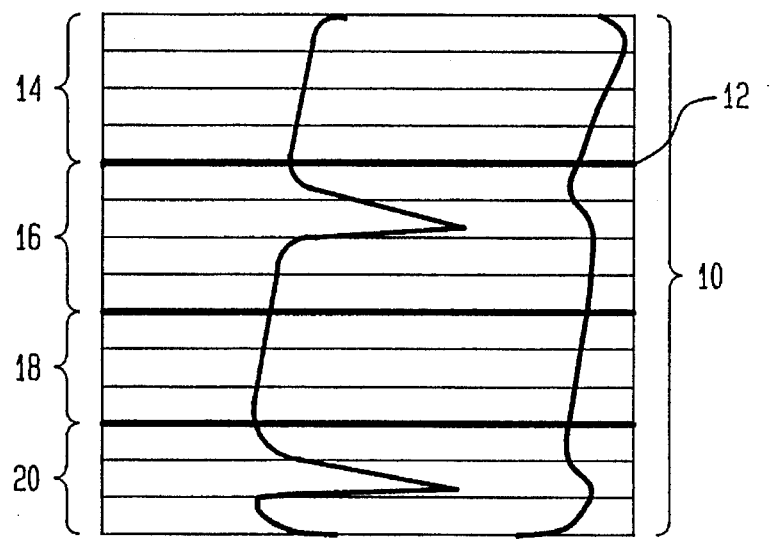
FIG. 1 a diagrammatic side view MIP of an entire image stack according to a prior art editing method.

Referring now to FIG. 1. the selection of the slabs according to the prior art method is made by displaying a side view MIP of the entire image stack 10 under study and selecting the borders 12 of the slabs 14, 16, 18, and 20 by pointing to their locations in the image stack 10. The top MIP image of each slab is computed by applying the MIP algorithm to the data making up the images of the slabs. The resulting top MIP images are characterized by the fact that they display the structures with the highest pixel intensity values. This is useful in identifying these structures in the images.

Figure 2:
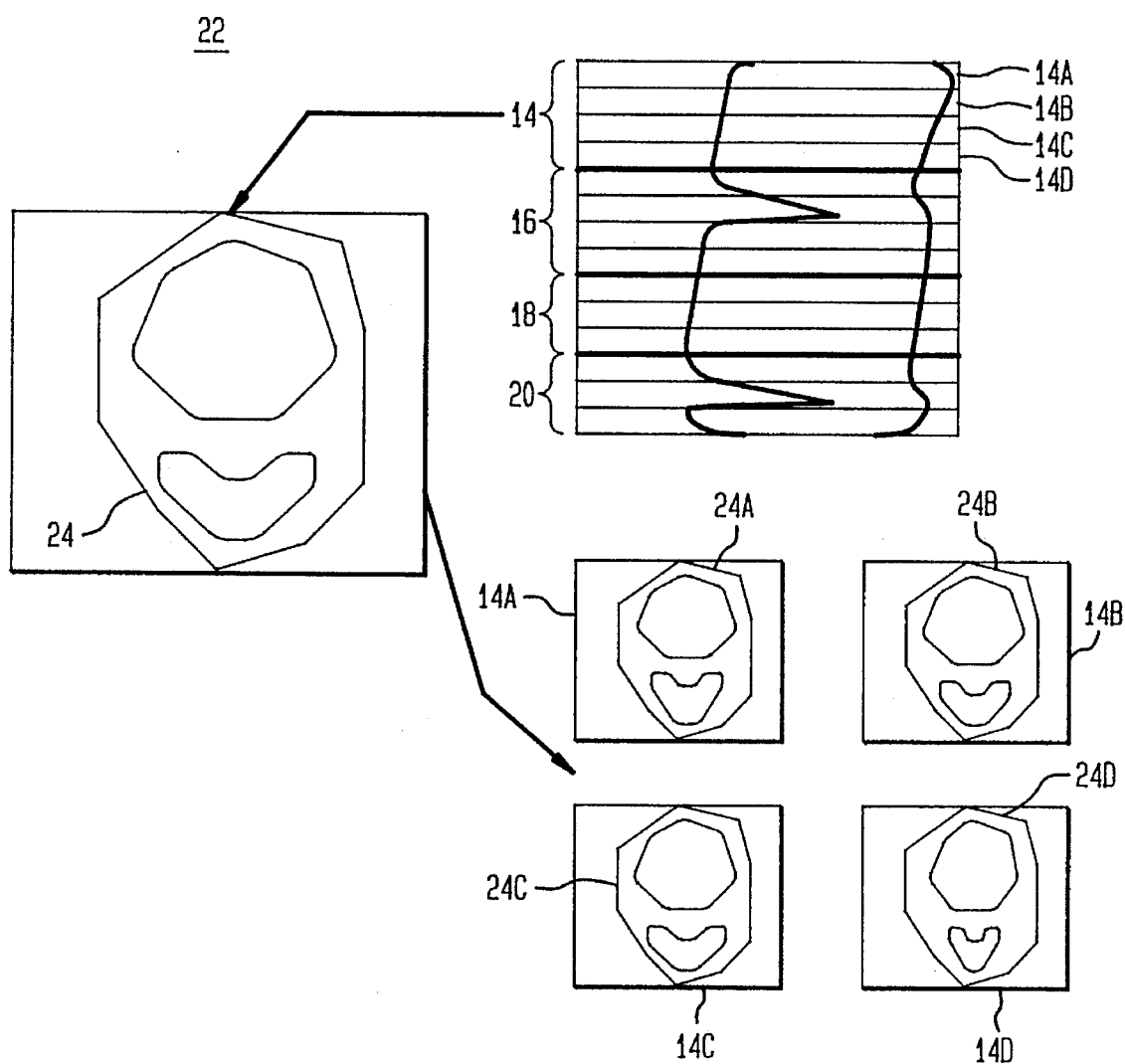
FIG. 2 illustrates the prior art method for editing images of each slab.

FIG. 2 illustrates the prior art method for editing the images of one of the slabs shown in FIG. 1. In FIG. 2, the user manually performs modifications on the top MIP image 22 of the top slab 14. These modifications are then applied to images 14A, 14B, 14C and 14D of the slab 14 from which the top MIP image 22 is derived. The top MIP image can be modified in a number of ways. As already mentioned, the user can manually draw contours around the regions to be removed as shown in FIG. 2. The individual images can also be modified to supplement the modifications of the top MIP image. As the slabs 14, 16, 18 and 20 are traversed, the current slab inherits the contours of the previously modified slab. Thus, the user can adjust the inherited contours on the top MIP image of the third slab instead of having to draw them from scratch.

Figure 3B:
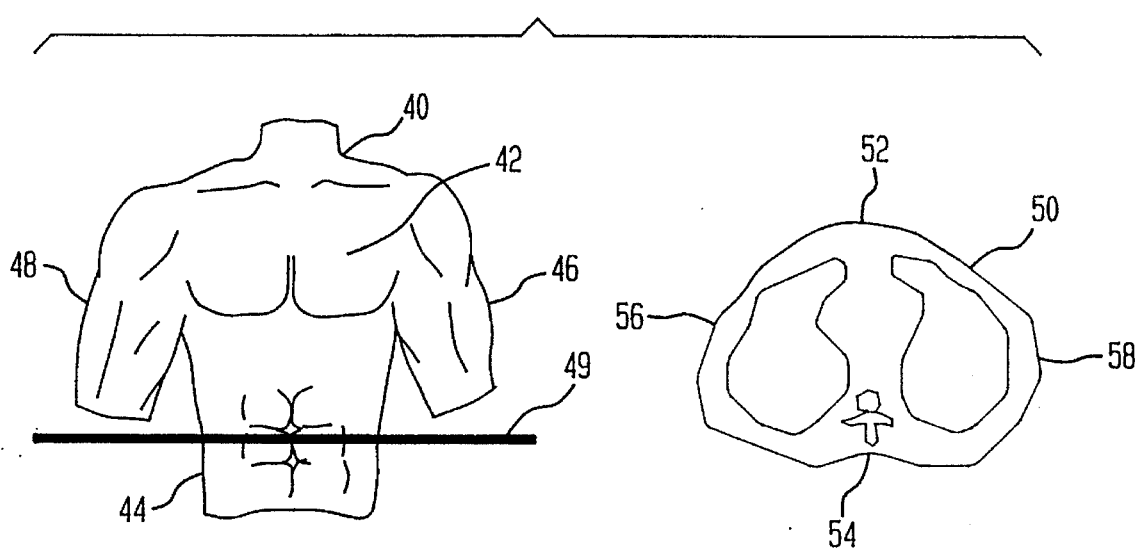
FIG. 3B illustrates the image orientation as it relates to a patient's position according to the present invention.
Figure 3A:
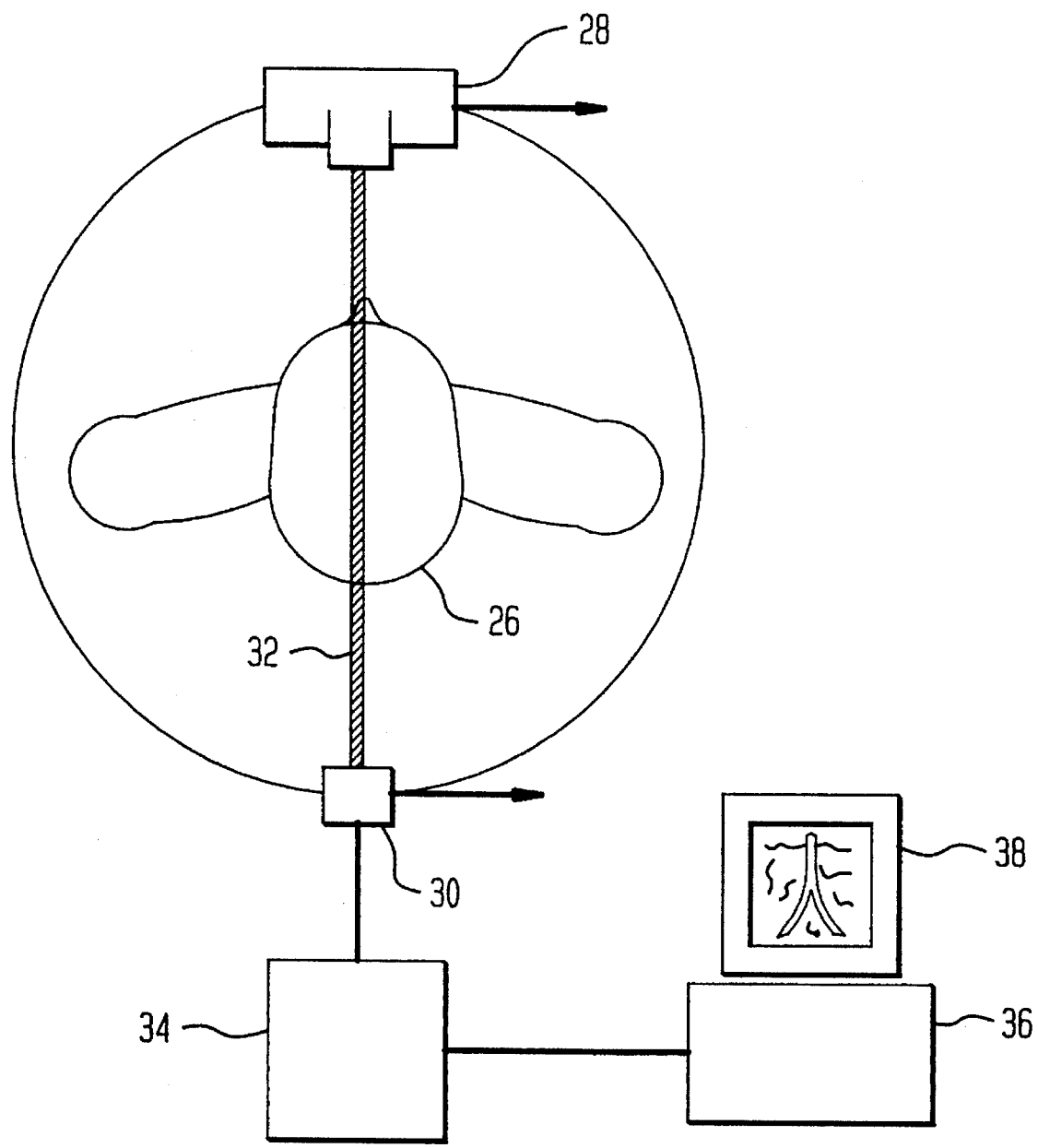
FIG. 3A illustrates a basic CT scanning system for carrying out the method according to the present invention.

With the above defined concepts in mind, the method and apparatus for automatically editing images used in abdominal 3D-CT angiography according to the present invention will now be described. The basic CT scanning system apparatus for carrying out the method according to the present invention is well known in the art and generally comprises, as shown in FIG. 3A, an x-ray tube 28 and a radiation detector 30. As is well known in the art, in order to generate an image of a body slice of interest, the x-ray tube 28 projects a thin x-ray beam 32 through the object slice of the subject 26 under study. The attenuation of the x-ray beam 32 is determined for a large number of paths through the object slice. The radiation intensity is recorded by the detector 30 for each path through the object slice. The detector 30 is coupled to a measurement electronics device 34 which codes the measurement values sensed by the detector 30 into a suitable form. The measurement electronics device 34 is coupled to a computer 36 which processes the coded measurement values and calculates a two or three dimensional attenuation distribution. The attenuation distribution generally comprises a numerical matrix which is stored by the computer 36.

The computer 36 is coupled to a television monitor 38 which converts the numerical matrix into an image which can be viewed by the operator. Each point or pixel of the image corresponds to a matrix element. As is well known in the art, the illuminating intensity value of each pixel represents the amount of attenuation cause by the objects scanned in the object slice.

In any event, the first item that must be establish concerns the orientation of the image relative to the patient's position. FIG. 3B, shows how the image 50 is oriented relative to the patient's 40 position. The CT image is obtained from a transverse plane 49 which has no large oblique angles in either the patient or in the transverse plane. The patient's 40 orientation with respect to the image according to the present invention is as follows: the patient's anterior 42 is the top side 52 of the image 50; the patients' posterior 44 is on the bottom side 54 of the image 50; the patient's right side 48 is the right side 58 of the image 50; and the patient's left side 46 is the left side 56 of the image 50.

Figure 4:
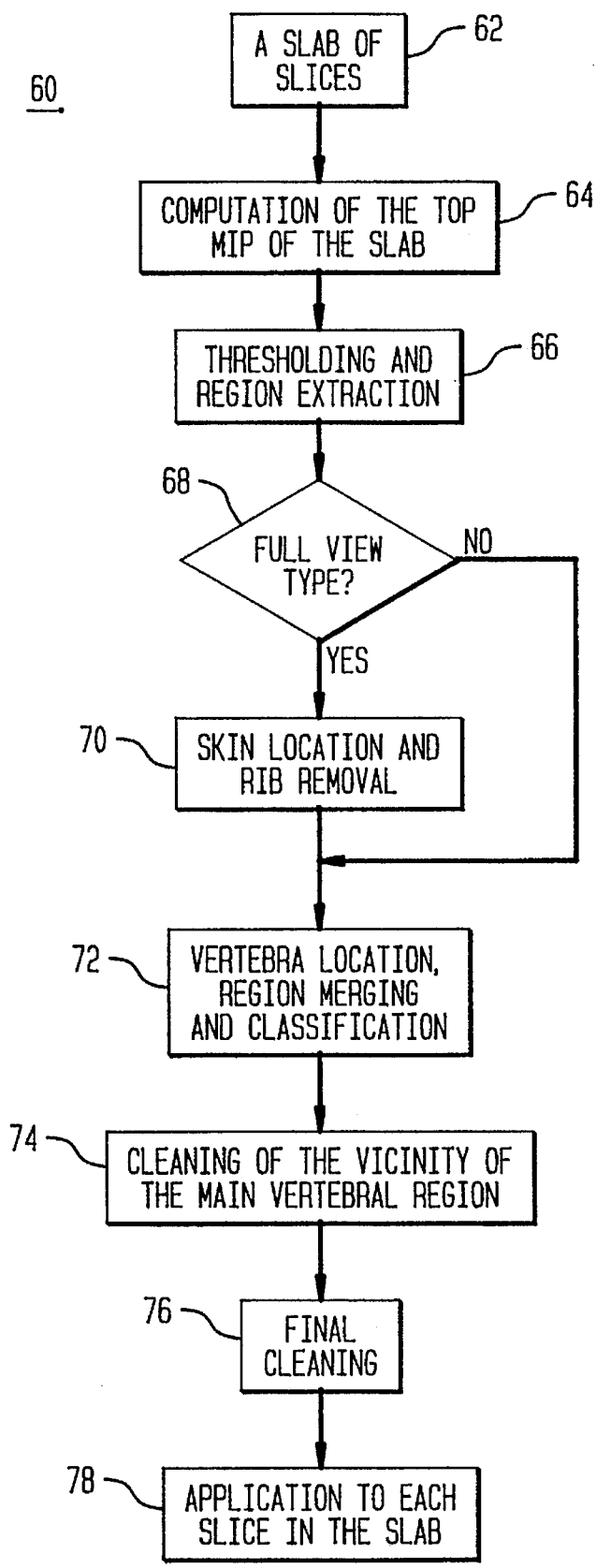
FIG. 4 is a flowchart depicting an overview of how the software package operates to provide automatic editing of abdominal CT images according to the present invention.

The general objective of editing abdominal CT images for blood vessel visualization is to remove the bone structures in each image slice and leave blood vessels and other tissues and organs substantially intact. The apparatus shown in FIG. 3A is operated and controlled via a novel software package which enables the operator of the system to automatically edit abdominal CT images for 3D blood vessel visualization. The software package is designed to be "user friendly" in meeting the needs of the operator. A flow chart 60 depicting an overview of how the software package operates to provide automatic editing of abdominal CT images for 3D blood vessel visualization is shown in FIG. 4.

Starting at the top of the flowchart, a top MIP image 64 of a slab 62 under study is computed. The information pertaining to the region of interest in the top MIP is then thresholded and extracted 66. A decision 68 is then made to determine whether the CT image is a full-view type. If the CT image is a full-view type, then skin location and rib removal 70 must be performed before vertebra location, region merging and classification 72 is performed. Next, the vicinity of the main vertebral region is edited or "cleaned" 74. Then a final editing or "cleaning" 76 operation is performed. After final editing, the application 78 of these modifications are made to each slice in the slab. A more detailed discussion of these operation follows immediately below.

Figure 5A:
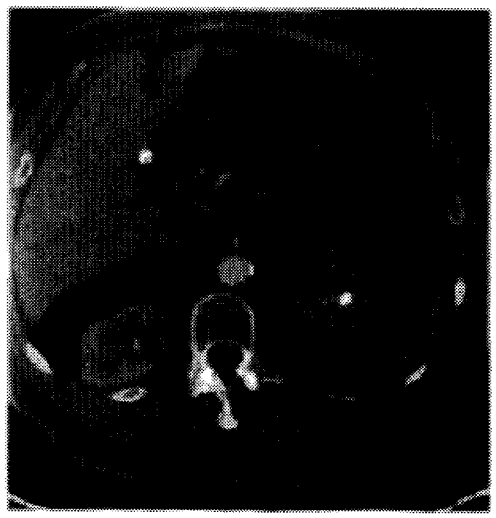
FIG. 5A illustrates a single original image slice.
Figure 5B:
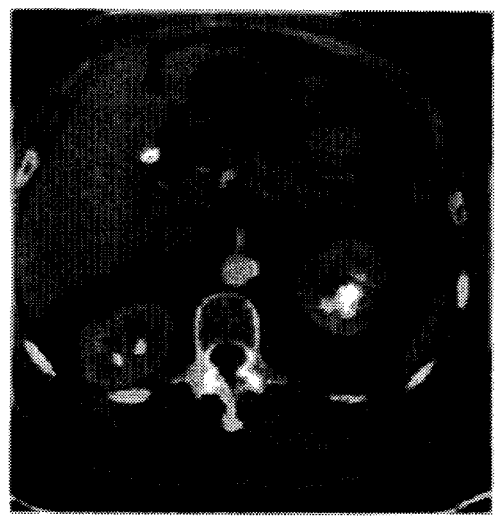
FIG. 5B illustrates a top MIP image from a slab of CT image slices.

The reason for computing a top MIP of a slab under study is that the pixel intensity distribution of the bone area of each individual slice is typically not uniform enough for a single threshold. This situation is alleviated by using a top MIP image from a slab composed of several consecutive slices. The result of this operation is demonstrated in FIGS. 5A and 5B where FIG. 5A shows a single original slice and FIG. 5B shows a top MIP image from a slab comprising 6 slices. As can be seen by comparing FIGS. 5A and 5B, there are some bones that show up in the top MIP image of FIG. 5B that are not visible in the single original slice shown in FIG. 5A.

In order to determine the correct number of slices in a given slab, a side MIP image is computed. From the side MIP image, the proper number of slices per slab can be determined by the operator. Alternatively, an empirical number of slices can be used to form a slab.

Once the top MIP image of the slab is computed the process of editing bone tissue from the slices is commenced by performing a thresholding and region extraction step. Thresholding is performed on the top MIP image of the slab. The user selects a threshold which operates to roughly separate the blood vessels from the vertebral body. The top MIP image is thresholded by selecting a particular pixel intensity value. Once the threshold is selected all pixels having an intensity value below the selected threshold value are set to zero, i.e. turned dark. Next, the pixel with the highest intensity value is selected as a seed and a flood filling algorithm is performed to catch regions having pixels with zero intensity as their boundary. For a discussion of flood filling algorithms, reference can be made to an a book entitled COMPUTER GRAPHICS by J. D. Foley et al., published by Addison-Wesley, 1990.

When a region is flooded, the pixel intensity values in the region are converted into a value which is lower than the selected threshold value. Then, another pixel with the highest intensity value is selected from another region and the flood filling algorithm is applied to catch that region. The flood filling algorithm is repeatedly applied until no more pixels above the selected threshold can be found. The information of each region such as the boundary, the area, and the bounding box is subsequently extracted for further processing.

Figure 6A:
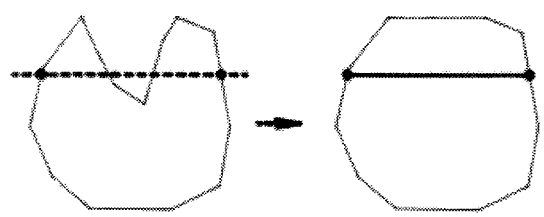
FIG. 6A presents a graphical illustration of horizontal adjustment.
Figure 6B:
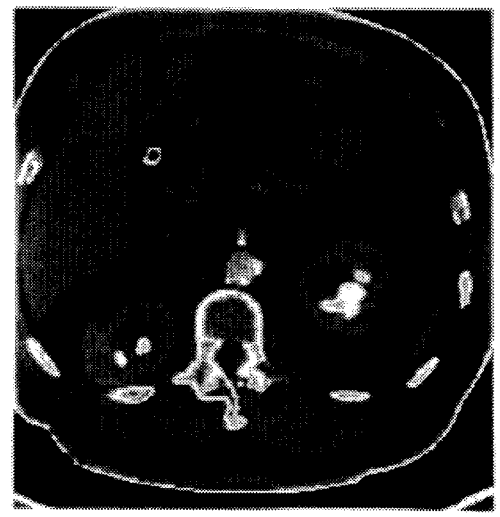
FIG. 6B illustrates the top MIP image after the thresholding and region extraction steps have been performed.

The shape of an extracted region is sometimes jagged or has small holes inside which result from unidentified regions. Since there are no blood vessels within the bone region, the unidentified regions are adjusted or filled in by the flood filling algorithm when thresholding and region extraction is performed. As can be seen by referring to FIG. 6A which presents a graphical explanation of horizontal adjustment, the flood filling algorithm fills in the unidentified regions by detecting the leftmost and the rightmost boundary points in every row in a region. The two points and the horizontal line segment therebetween are considered inside the region regardless that some points may not belong to the region in the original detected boundary. The top MIP image after thresholding and region extraction is performed can be seen in FIG. 6B.

Figure 7A:
FIG. 7A illustrates a zoom-in view type of CT image.
Figure 7B:
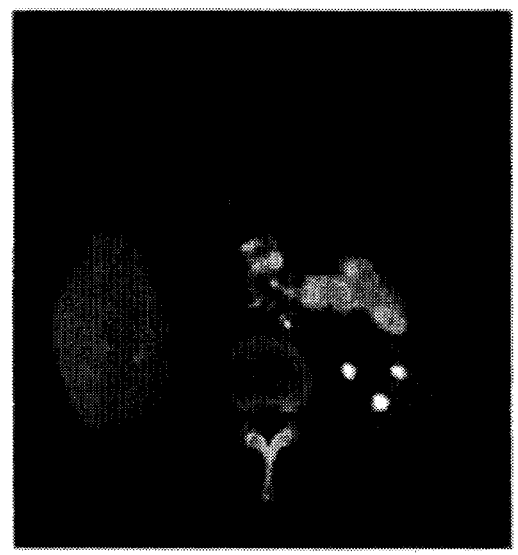
FIG. 7B illustrates a full-view type of CT image.

At this stage of the method it should be noted that two types of CT images of the abdomen area are distinguished in the present invention. The first type of CT image is depicted in FIG. 7A, and is characterized by a zoom-in view which typically includes only the vertebra. It should be noticed that the skin can not be seen in this view. The second type of CT image is depicted in FIG. 7B, which shows a full view of the abdomen where most of the skin can be seen. This is an important distinction because if skin can be seen in the image as is the case with CT images are of the second type, then ribs are also visible in the image since they are located immediately adjacent the skin.

Thus, the skin location and rib removal steps described herein are only applicable if the CT image is of the second type since it provides a full view image where the ribs are visible and must be removed. Since the ribs generally lie within a certain distance beneath the skin, the skin is located first, in order to remove the ribs. Any image having at least the anterior and posterior skin visible is considered a full view image. Since the intensity value of the background outside the torso is very low, a low threshold is set to separate the background from the torso. The skin is then traced out by detecting the boundary between the background and the torso. After the skin is obtained, the geometric center of the skin is calculated. Each point on the skin and the center form a vector. A new contour is derived by shrinking all the vectors by a predetermined amount. The region enclosed by the new contour and the skin includes all of the ribs.

The regions detected above are merged and classified based on the following observations and anatomical assumptions:

The image orientation is as shown in FIG. 3B.

The vertebral body is generally round in shape.

The vertebra are located near the bisector of the image.

No bones are above the vertebral body or within a range to skin if skin is visible.

No blood vessels are below the vertebra.

The rest of the bone regions are smaller than the vertebral body.

Within a certain range, no bones are in the areas on the left and right hand sides of the vertebral body.

Ribs are close to the skin in the left and right side of the image if skin is visible.

Figure 8A:
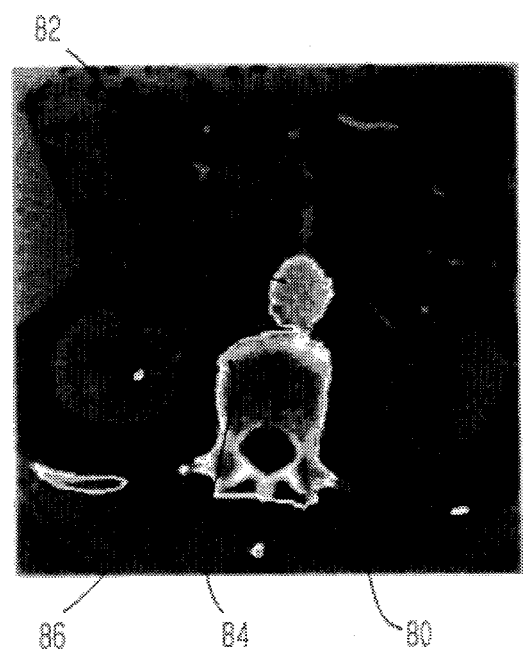
FIG. 8A illustrates a situation where blood vessels are immediately adjacent to the vertebral body.
Figure 8B:
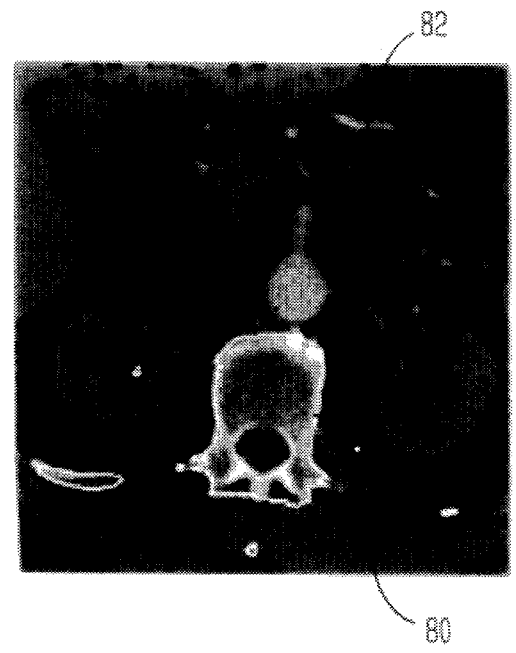
FIG. 8B illustrates the blood vessel of FIG. 8A as it is separated from the vertebral body.

The location of the vertebral body is determined in the vertebra location step by identifying a region with a large highly illuminated area which is located near the vertical bisector of the image. In some situations, blood vessel regions are immediately adjacent to the vertebral body as shown in FIG. 8A. In order to distinguish the vertebral body 80 from a blood vessel 82, the top section of the vertebral body 80 is examined to determine whether there is a substantially round region. When the top section of the vertebral body 80 has a blood vessel 82 immediately adjacent to it, the blood vessel 82 can be identified by a substantially round region that extends from the top of a contour 84 via a bottle neck 86. The bottle neck 86 forms the shortest horizontal line segment in the middle portion of the top section. When such a round region is identified, it is considered a blood vessel 82 and is separated from the vertebral body 80 as shown in FIG. 8B.

Once the vertebral body is detected, the regions closely adjacent to it are selectively merged in to it. The merge operation uses an overlapped ratio of bounding boxes, relative positions, relative distances, and shape information to determine whether a region must be merged into the main region of the vertebral body. In the present invention, a bounding box is defined as a rectangle having its four sides touched by the extremes of a contour in the vertical and horizontal directions. Relative distance is defined as the shortest straight line distance between two contours. Relative position is defined as the relative position of the bounding boxes of two contours.

The region merging and classification steps are performed according to the following rules which are divided into three categories as set forth below.

The first rule category relates to regions that are larger than the main vertebral region. Referring to FIG. 9A, if the shape of the bounding box 88 of the main region is narrow (i.e., the ratio of width to height of the bounding box is less than ½), the regions on the two sides of the main region are most likely part of the main region. Therefore, these regions are not classified at this point and are merged into the main region 90 as shown in FIG. 9B. Furthermore, all other regions are considered non-bone regions. If, however, the shape of the main region is not narrow as shown in FIG. 9C, then all the regions 92 larger than the main region are treated as non-bone regions notwithstanding their location.

Figure 10B:
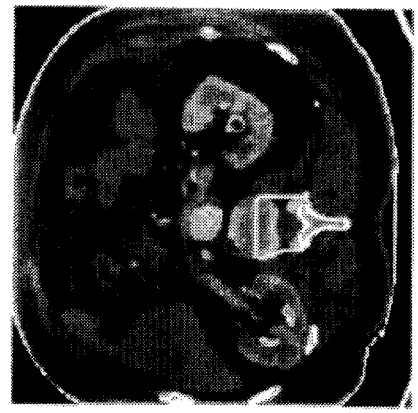
FIG. 10B is a graphical example of merging the region shown in FIG. 10A into the vertebral body.
Figure 10A:
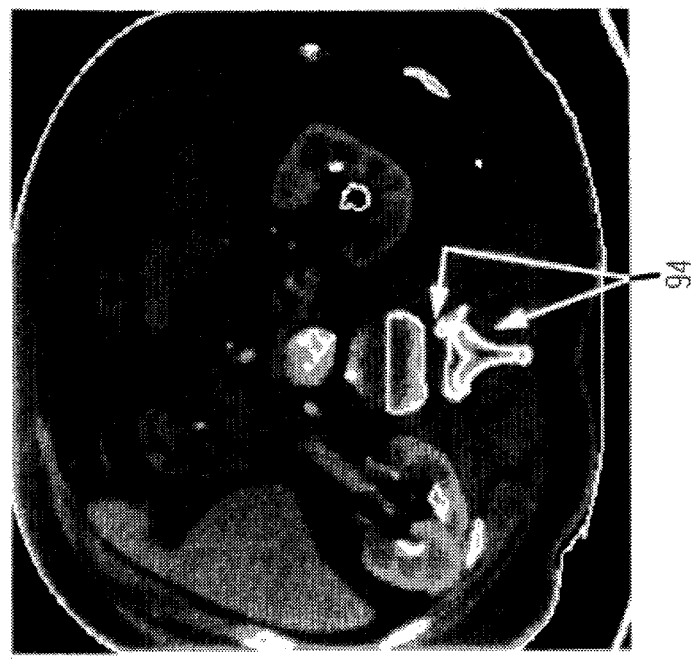
FIG. 10A is a graphical example of a region which lies below the vertebral body.
Figure 11A:
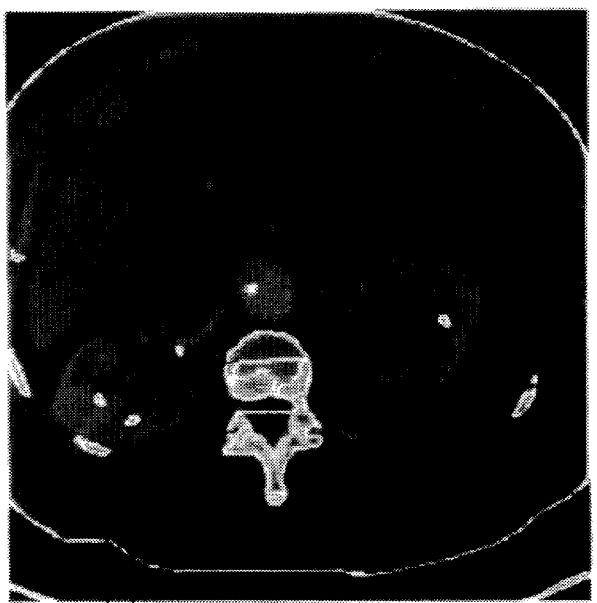
FIG. 11A is a graphical example of regions which lie directly above the main vertebral region.
Figure 11B:
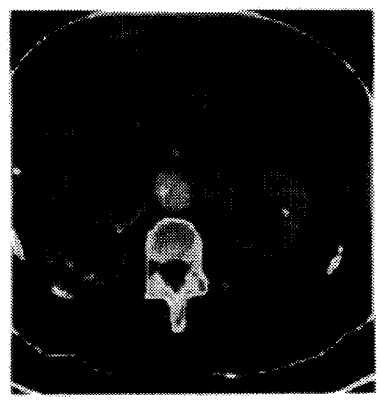
FIG. 11B is a graphical example of merging the regions shown in FIG. 11A into the main vertebral region.
Figure 12A:
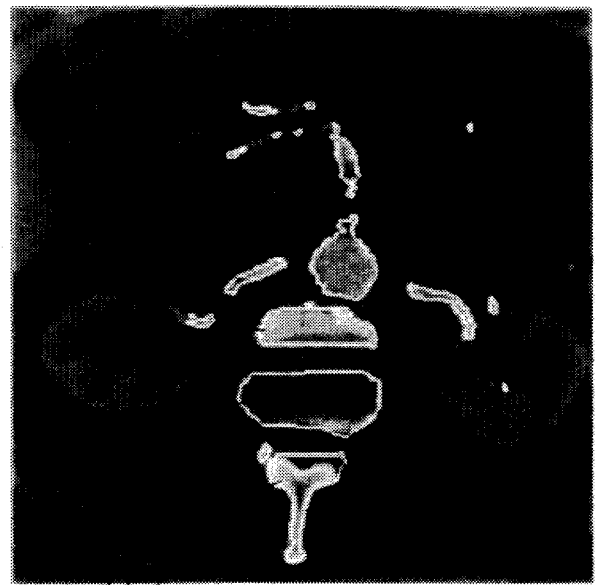
FIG. 12A is a graphical example of regions which are moderately spaced from the main vertebral region.
Figure 12B:
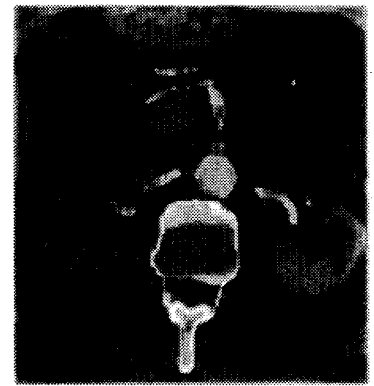
FIG. 12B is a graphical example of merging the regions shown in FIG. 12A into the main vertebral region.

The second rule category relates to regions that are smaller than and immediately adjacent to the main vertebral region. If these smaller regions 94 are directly below or not directly above the main region as shown in FIG. 10A, they are then merged into the main region as shown in FIG. 10B. If, however, the regions are directly above the main region and their bounding boxes 96 overlap the bounding boxes of the main region as shown in FIG. 11A, they are then merged into the main region as shown in FIG. 11B if the ratio of the overlapping portions and the non-overlapping portions is over ⅓. If the regions 98 are moderately spaced above the main region, the region closest to the main region is determined first. If the shape of this region is not substantially round and has a gap which is parallel to the main region as shown in FIG. 12A, then it is merged into the main region as shown in FIG. 12B.

Figure 13A:
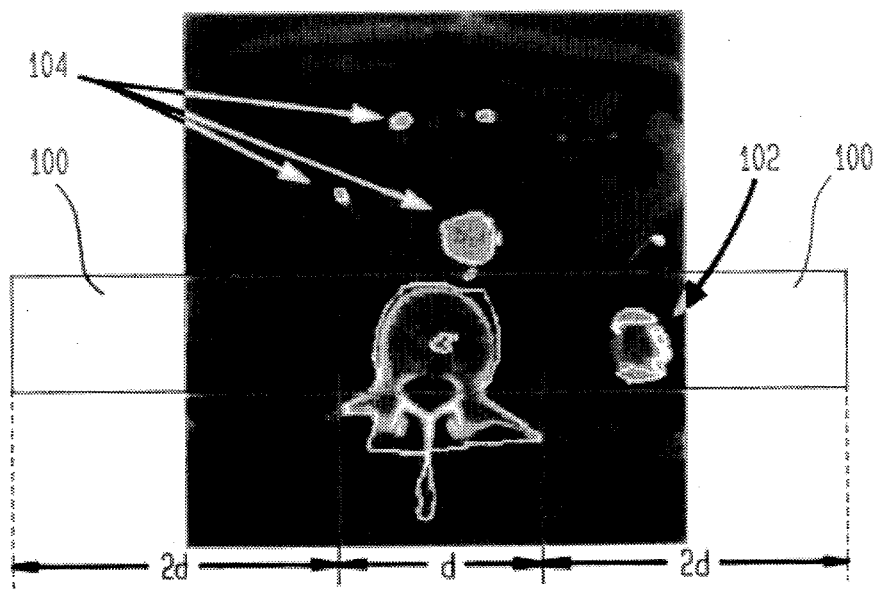
FIG. 13A illustrates region classification and merging as they relate to a zoom-in view type of CT image.
Figure 13B:
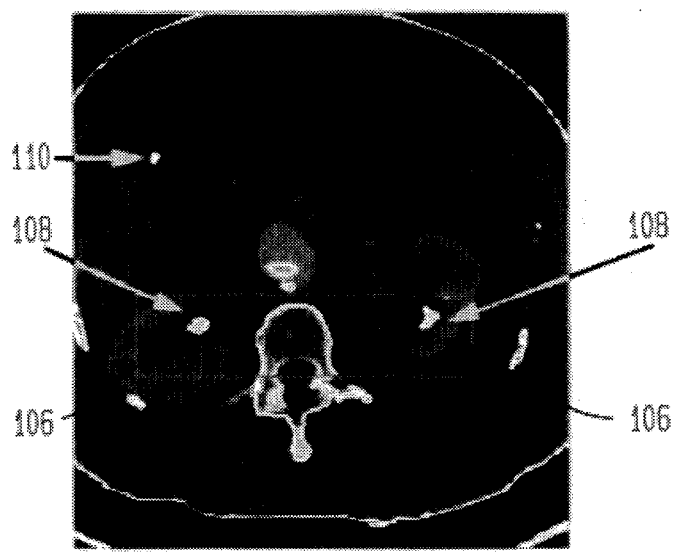
FIG. 13B illustrates region classification and merging as they relate to a full-view type of CT image.

The third rule category relates to regions that are smaller than, but not immediately adjacent to the main vertebral region. In order to identify the non-bone regions, an area 100 is defined on each side of the main region. The width of each area is made twice the width of the main region. Referring to FIG. 13A which illustrates when the images are of the zoom-in type, the regions 102 that lie inside the areas are classified as non-bone regions and the regions 104 that lie above the areas are classified as non-bone regions. Referring now to FIG. 13B which illustrates when the images are of the full view type, the regions 108 that are inside the areas 106 are classified as non-bone regions. The regions 110 that are outside the areas 106 but not immediately adjacent to skin are classified as non-bone regions.

Figure 14B:
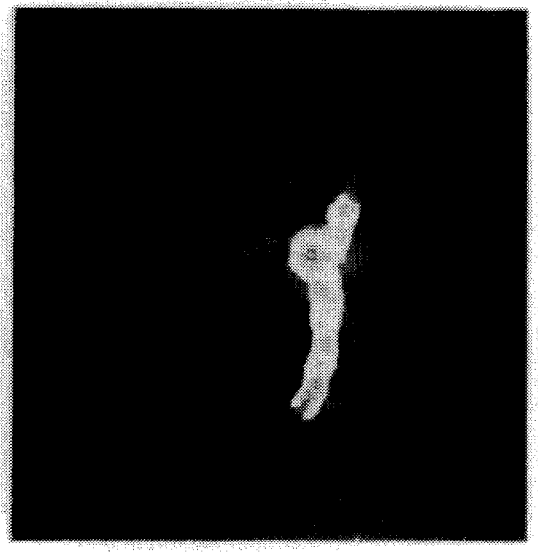
FIG. 14B illustrates a top MIP image after vertebral body location, classification and merging.
Figure 14A:
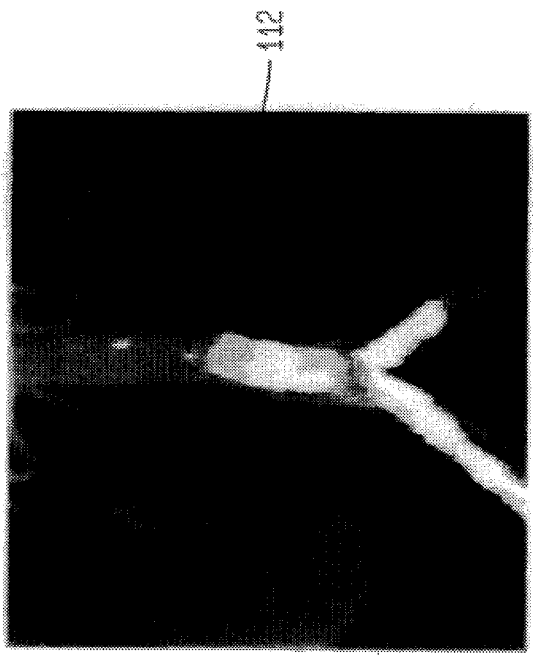
FIG. 14A illustrates a side MIP image after vertebral body location, classification and merging.

The above-described steps produce generally good side MIP images as shown in FIG. 14A, because most of the bones are removed and the intensities of the residues are smaller than that of the blood vessels 112. The top MIP image, however, results in an unacceptable view as shown in FIG. 14B, if residues still remain along the borders of the removed bone regions. This is due to the fact that in this particular viewing angle, the residues have the highest intensity along those projection lines and therefore, stand out very clearly. Moreover, the remaining pixels along the projection line have been set to a low value since the bone regions have been removed in the majority of the slices.

Figure 15A:
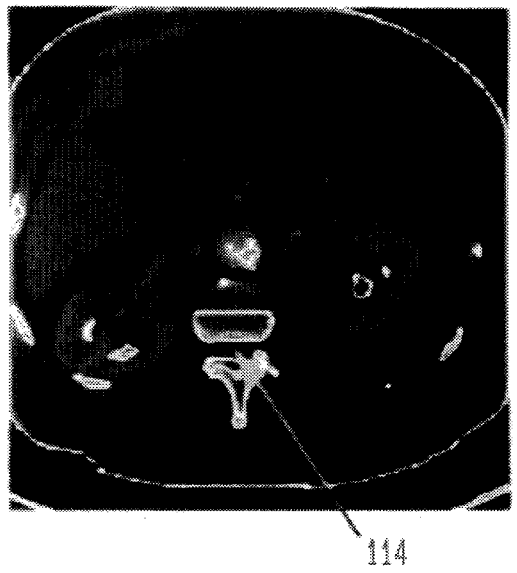
FIGS. 15A and 15B demonstrates the use of a pseudo mask and fan out mask where
Figure 15B:
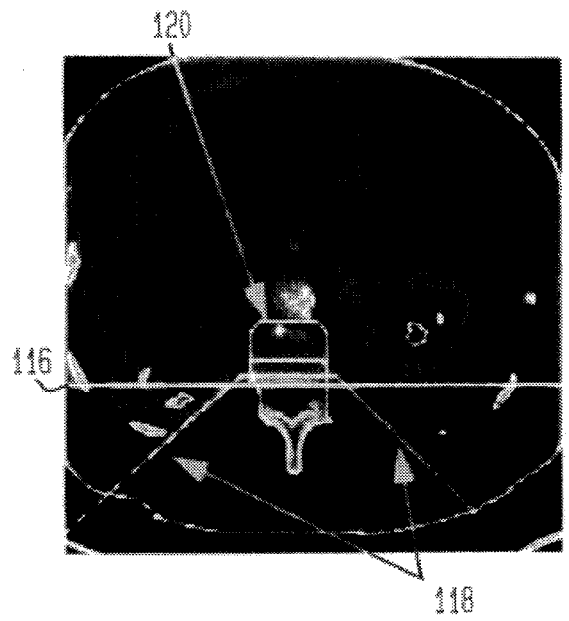

In order to improve the view of the top MIP image further editing is performed as follows. Referring now to FIG. 15A, the vertebral canal 114 is visible through out all of the abdominal images of a particular study, thus, it is regarded as a stable feature in the method of the present invention. It is, therefore, located by searching in the vertical direction along the central line of the main body region designated the boundary line 116 as shown in FIG. 15B. The boundary line 116 is considered the point where there is a large intensity drop along the searching line. The boundary line 116 separates the main vertebral region into two parts. The upper portion contains the vertebral body and the lower portion contains the remaining portions of the vertebral body such as laminae and spinous process. All the residues in the lower portion are edited out by a fan-out mask 118 which extend down from the boundary line 116. The fan-out angle has been adapted to cover all the residues located below the vertebral body. The vertebral body located in the upper portion, has a stable shape. Whenever there is an incomplete vertebral body, a pseudo body shaped mask 120 is used to mask out that region. The pseudo body shape is derived by taking the width and height ratio of a normal vertebral body shape of the particular case under study. The bones detected in the regions described above are then masked out by changing the intensity values of the pixels in those regions to a very low value such as zero.

Figure 16:
FIG. 16 illustrates the final edited image of the image shown in FIG. 5A.
Figure 17A:
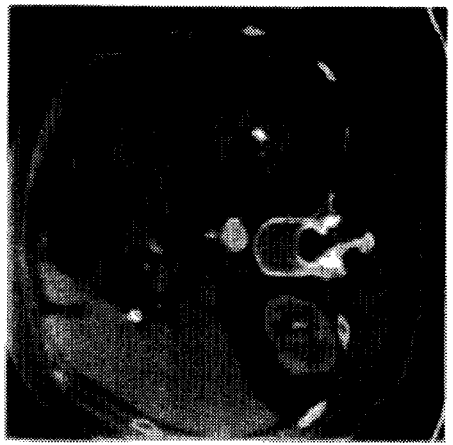
FIGS. 17A–17I and 18A–18I illustrate case studies which demonstrate the benefits of the present invention as applied to the full view type of CT image.
Figure 17B:
Figure 17C:
Figure 17D:
Figure 17E:
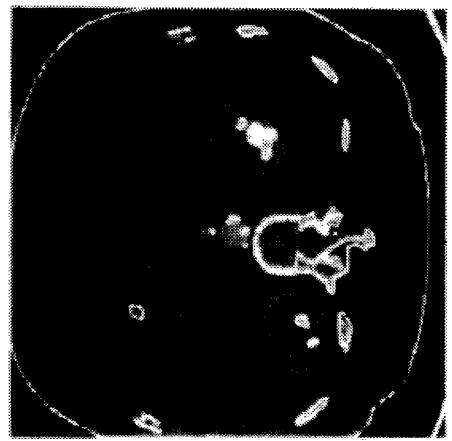
Figure 17F:
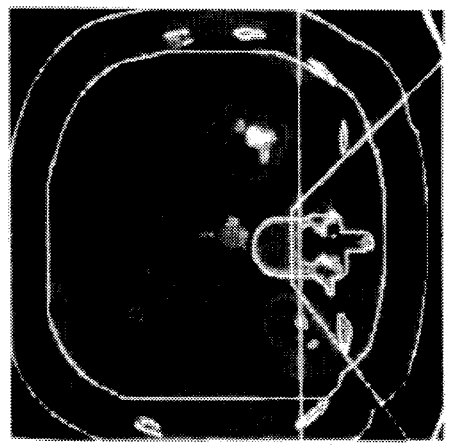
Figure 17I:
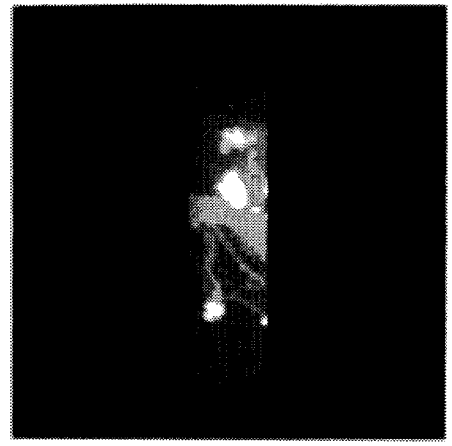
Figure 18C:
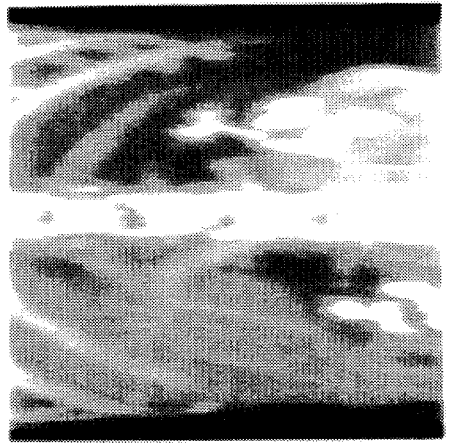
Figure 17H:
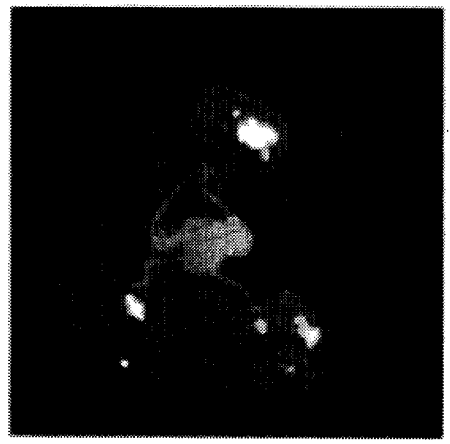
Figure 18B:
Figure 17G:
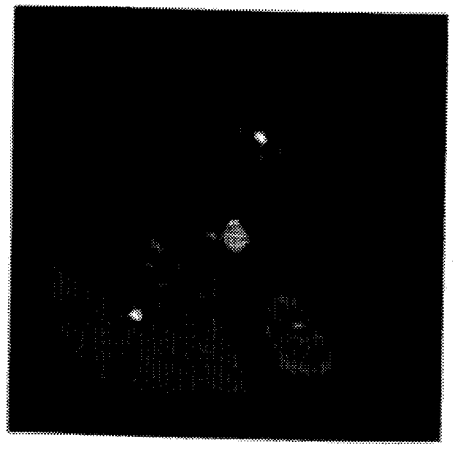
Figure 18A:
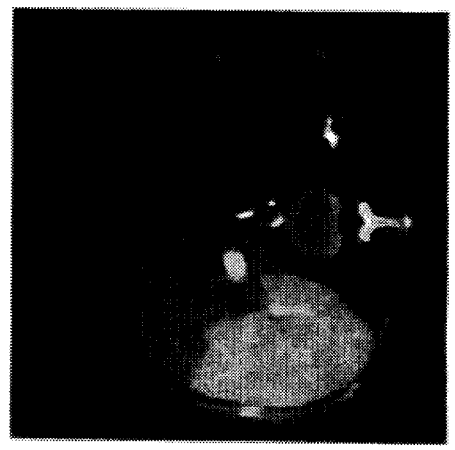
Figure 18F:
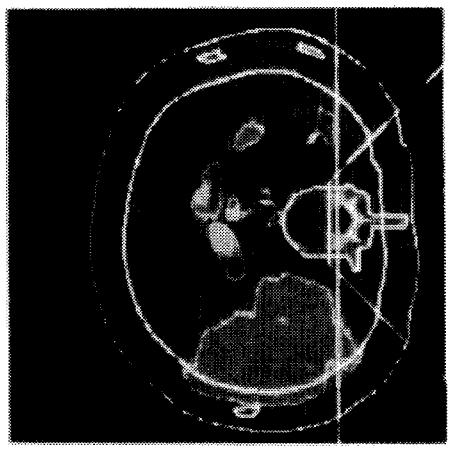
Figure 18I:
Figure 18E:
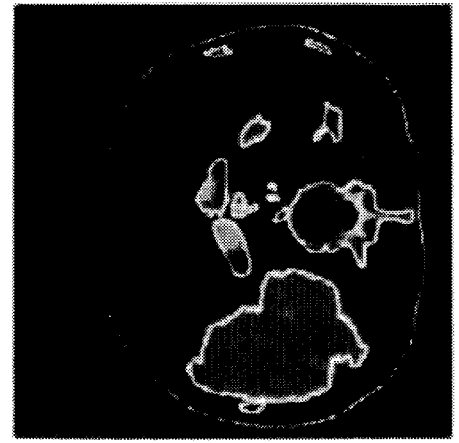
Figure 18H:
Figure 18D:
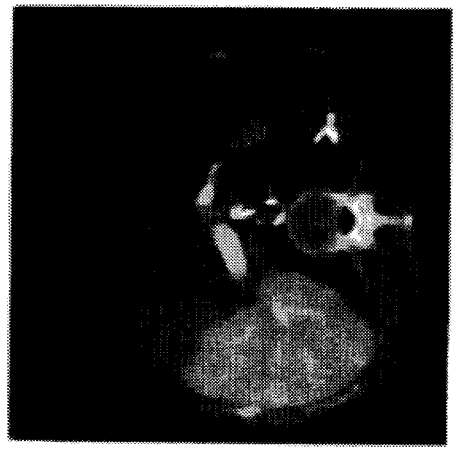
Figure 18G:
Figure 19C:
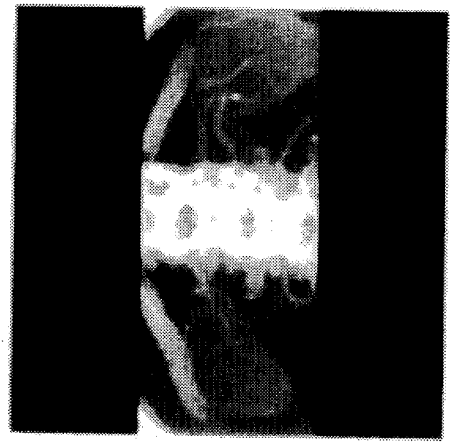
FIGS. 19A–19I and 20A–20I illustrate case studies which demonstrate the benefits of the present invention as applied to the zoom-in type of CT image.
Figure 19F:
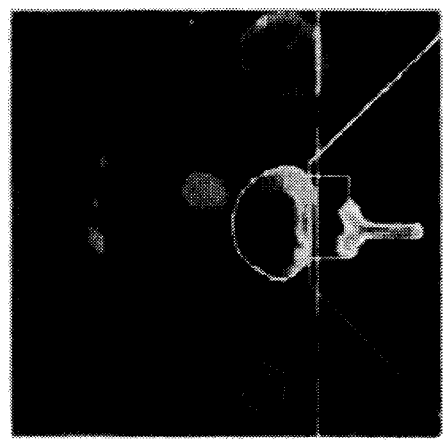
Figure 19B:
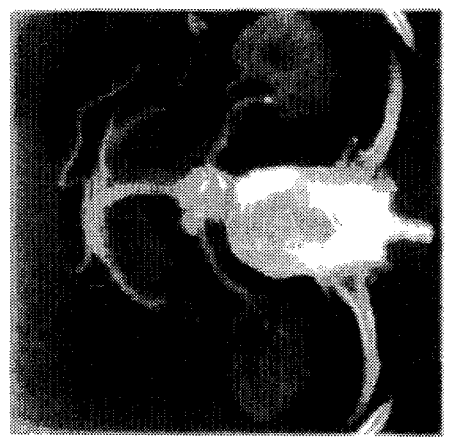
Figure 19E:
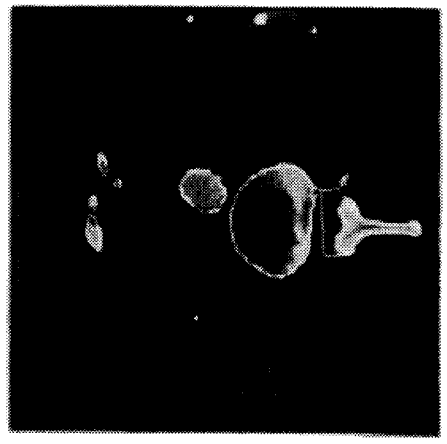
Figure 19A:
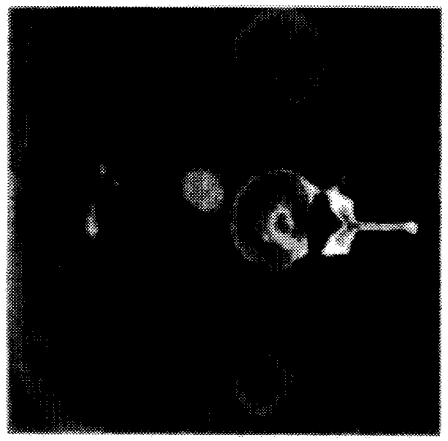
Figure 19D:
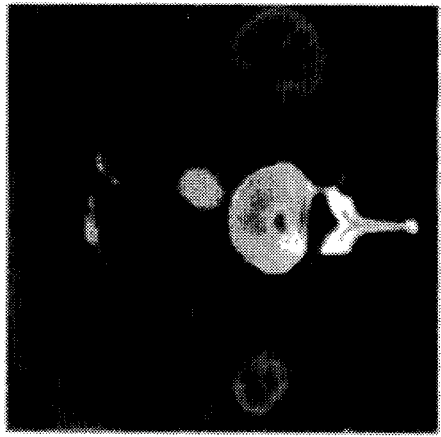
Figure 19I:
Figure 19H:
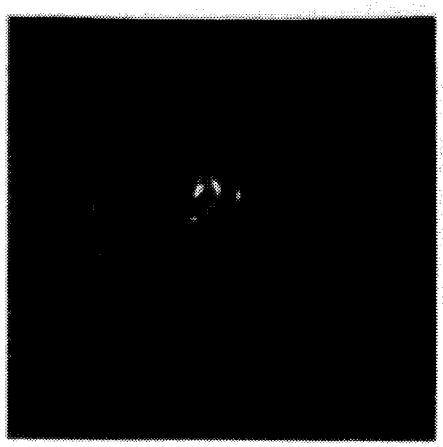
Figure 19G:
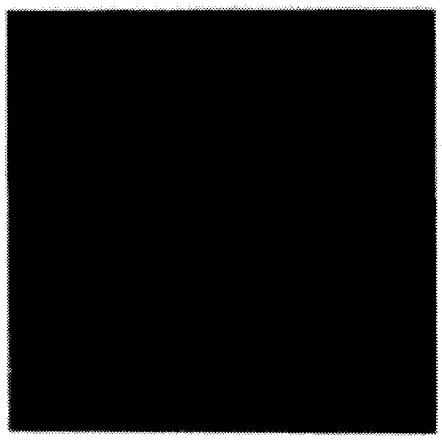
Figure 20C:
Figure 20B:
Figure 20A:
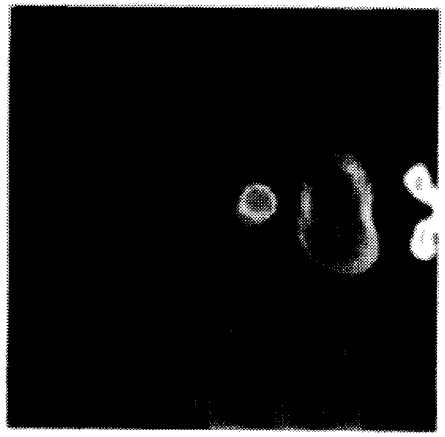
Figure 20F:
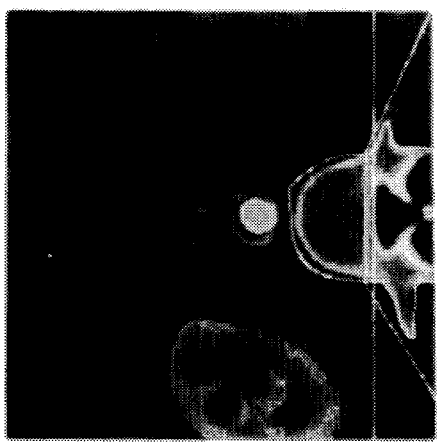
Figure 20I:
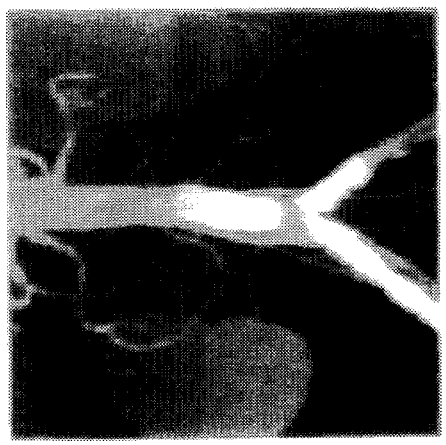
Figure 20E:
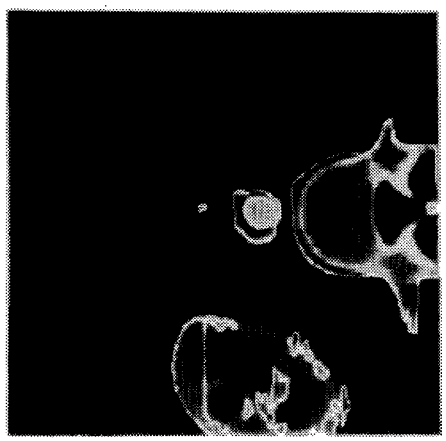
Figure 20H:
Figure 20D:
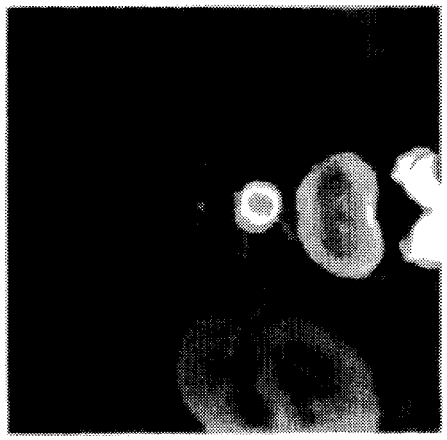
Figure 20G:
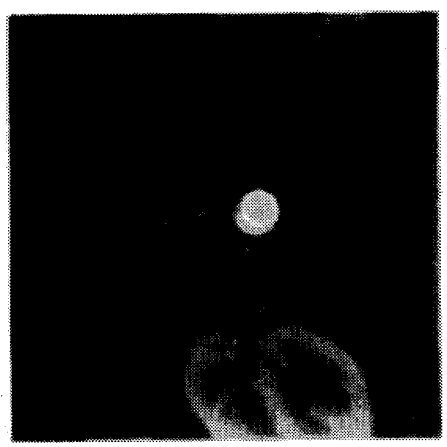

The final editing step according to the present invention will now be described with reference to FIG. 16. After completing the editing steps above, some residues may still be remaining along the boundary of the bones. Thus, a final editing step is performed along the boundaries with a 5 by 5 square binary mask as shown in FIG. 16 which shows a "bone removed" image of FIG. 5A.

Once the modifications to the top MIP of the slab under study have been completed, the modifications are then applied to the individual slices of the slab as discussed earlier in connection with the prior art editing method.

TEST RESULTS

In order to demonstrate the benefits of the present invention, images from four different case studies are presented. Two of these case studies demonstrate the benefits of the present invention as applied to the full view type of CT image. These case studies are depicted in FIGS. 17A–17I and 18A–18I. The other two case studies demonstrate the benefits of the present invention as applied to the zoom-in type of CT image. These case studies are depicted in FIGS. 19A–19I and 20A–20I.

In FIGS. 17A, 18A, 19A, and 20A, reference can be made to the original unedited sample slices. A top MIP image from the original slices is shown in FIGS. 17B, 18B, 19B, and 20B. FIGS. 17C, 18C, 19C, and 20C show a side MIP from the original slices. A typical slab top MIP image is shown in FIGS. 17D, 18D, 19D, and 20D. FIGS. 17E, 18E, 19E, and 20E show a processed image after segmentation and region extraction. FIGS. 17F, 18F, 19F, and 20F show a final processed image. A slice with bone removed is shown is FIGS. 17G, 18G, 19G, and 20G. A top MIP image from slice with bone removed is shown in FIGS. 17H, 18H, 19H, and 20H. FIGS. 17I, 18I, 19I, and 20I show a side MIP image from slices with bone removed.

It should be apparent from comparing the side MIP images of the originals to the side MIP images showing the bone removed slices, that great improvements in blood vessel visualization have been achieved by the present invention. These improvements come with an increase in the speed and efficiency of the editing process which reduces the overall cost of operator and machine time.

It should be understood that the embodiment described herein is merely exemplary and that a person skilled in the art may make many variations and modifications to the embodiment as described herein. Any and all such variations or modifications as well as others which may become apparent to those skilled in the art, are intended to be included within the scope of the invention as defined by the appended claims.

I/we claim:

1. A method for automatically editing a plurality of computed tomograms to provide a three dimensional view of a selected object located within a patient's body, each of said computed tomograms comprising an array of pixels having various illuminating intensities which depict various objects scanned by a computed tomogram scanning system within a layer of a patient's body, said method comprising the steps of:

providing at least one slab of computed tomographic image slices produced by said computed tomogram scanning system, said image slices including an undesirable object;

computing a top maximum intensity projection of said slab;

automatically removing said undesirable object from said top maximum intensity projection of said slab in order to define modifications to be applied to said image slices of said at least one slab; and applying said modifications to each computed tomographic image slice in said at least one slab in order to remove said undesirable object from said image slices.

2. The method according to claim 1, wherein said step of automatically removing said undesirable object further comprises the steps of:

selecting a given threshold illuminating intensity value whereby pixels representing said undesirable object to be removed is set to substantially zero if the illuminating intensity value of said pixels are below said threshold illuminating intensity value;

selecting a pixel having the highest illuminating intensity value; and performing a flood filling algorithm to seize a region having pixels with an illuminating intensity of substantially zero defining said region's boundary, said region representing said undesirable object to be removed.

3. The method according to claim 1, wherein said selected object to be viewed comprises blood vessels, organs and non-bone tissue and said undesirable object to be removed comprises bone tissue.

4. The method according to claim 3, wherein said bone tissue comprises a main vertebral region which includes a vertebral canal defined by a vertebral body, laminae and a spinous process.

5. The method according to claim 3, wherein said at least one slab of computed tomogram images are zoom-in view images and said bone tissue consists essentially of a main vertebral region which includes a vertebral canal defined by a vertebral body, laminae and a spinous process.

6. The method according to claim 3, wherein said at least one slab of computed tomogram images are full view images and said bone tissue comprises a main vertebral region and ribs, said main vertebral region including a vertebral canal defined by a vertebral body, laminae and a spinous process.

7. The method according to claim 4, wherein said step of automatically removing said undesirable object further comprises the steps of:

detecting said vertebral body;

classifying regions located adjacent to said vertebral body into regions comprising bone tissue of said vertebral body and regions comprising said blood vessels, said organs and said non-bone tissue; and merging said adjacently located regions which are classified as said bone tissue of said vertebral body into said vertebral body.

8. The method according to claim 7, wherein said step of automatically removing said undesirable object further comprises the step of:

utilizing said vertebral canal as a boundary line for separating said main vertebral region into an upper portion which includes said vertebral body and a lower region which includes said laminae and said spinous process; and removing residual bone tissue from said upper and lower regions of said main vertebral region by setting the illuminating intensity value of pixels in said upper and lower regions to substantially zero.

9. The method according to claim 8, wherein said step of removing residual bone tissue from said upper portion of said main vertebral region comprises the step of:

applying a fan-out mask which extends from below said boundary line, wherein the illuminating intensity value of pixels located within a region defined by said fan-out mask are set to substantially zero.

10. The method according to claim 8, wherein said step of removing residual bone tissue from said lower portion of said main vertebral region comprises the step of:

applying a pseudo vertebral mask which extends from above said boundary line, wherein the illuminating intensity value of pixels located within a region defined by said pseudo vertebral mask are set to substantially zero.

11. The method according to claim 1, wherein said step of providing at least one slab of computed tomographic image slices produced by said computed tomogram scanning system further comprises the steps of:

projecting energy into said layer of said patient's body;

detecting changes in said energy which are indicative of said various objects including said selected object located within said patient's body; and calculating said at least one slab of computed tomographic images from said changes in said energy.

12. The method according to claim 1, wherein said step of computing a top maximum intensity projection of said slab comprises the step of:

applying a maximum intensity projection algorithm to said at least one slab of computed tomographic image slices to produce said top maximum intensity projection of said at least one slab.

13. Apparatus for performing a 3D reconstruction of a plurality of computed tomographic angiographic images slices to visualize a selected object located within a patient's body, each of said computed tomographic image slices comprising an array of pixels having various illuminating intensities which depict various objects scanned by a computed tomogram scanning system within a layer of a patient's body, said apparatus comprising:

projecting means for projecting energy into said layer of said patient's body;

detecting means for detecting changes in said energy which are indicative of said various objects including said selected objected located within said patient's body, whereby said projecting means and detecting means operate to provide at least one slab of computed tomographic image slices; and automatic editing means for removing an undesirable one of said various objects from a top maximum intensity projection of a slab of said computed tomographic images slices to define modifications to be applied to said image slices of said at least one slab and applying said modifications to each of said image slices in said at least one slab in order to freely visualize the selected object.

14. The apparatus according to claim 13, wherein said projecting means comprises an x-ray tube and said energy comprises an x-ray beam.

15. The apparatus according to claim 14, wherein said detecting means comprises an x-ray beam detector which records the attenuation of said x-ray beam as said beam passes through said various objects of said body layer.

16. The apparatus according to claim 13, wherein said automatic editing means comprises a computer program.

17. The apparatus according to claim 13, further comprising coding means coupled to said detecting means for coding said changes in said energy detected by said detecting means and converting said changes into data which can be processed into said at least one slab of image slices.

18. The apparatus according to claim 17, further comprising computer means coupled to said coding means for processing said data into said at least one slab of image slices.

19. The apparatus according to claim 18, further comprising monitor means coupled to said computer means for displaying said process data as said at least one slab of image slices.

20. The apparatus according to claim 13, wherein said selected object comprises blood vessels, organs and non-bone tissue.

* * * * *